US007883887B2

(12) United States Patent
Takagi et al.

(10) Patent No.: US 7,883,887 B2
(45) Date of Patent: Feb. 8, 2011

(54) AUTOMATIC CELL CULTIVATION APPARATUS UTILIZING AUTOCLAVE STERILIZATION AND METHOD FOR USING THE SAME

(75) Inventors: Mutsumi Takagi, 5-2, Miyanomori Sanjo 10-chome, Chuo-ku, Sapporo-Shi, Hokkaido 064-0958 (JP); Katsumi Nakashima, Hyogo (JP); Toshihisa Doi, Hyogo (JP); Takamasa Ogata, Hyogo (JP)

(73) Assignees: Kawasaki Jukogyo Kabushiki Kaisha, Kobe-shi, Hyogo (JP); Mutsumi Takagi, Sapporo-shi, Hokkaido (JP)

( * ) Notice: Subject to any disclaimer, the term of this patent is extended or adjusted under 35 U.S.C. 154(b) by 897 days.

(21) Appl. No.: 11/257,950

(22) Filed: Oct. 25, 2005

(65) Prior Publication Data
US 2006/0151185 A1 Jul. 13, 2006

(30) Foreign Application Priority Data
Oct. 25, 2004 (JP) ............................. 2004-309295

(51) Int. Cl.
*C12M 1/00* (2006.01)
*C12M 3/00* (2006.01)
*A61L 2/08* (2006.01)
*A61L 2/00* (2006.01)

(52) U.S. Cl. .............. 435/303.1; 435/286.1; 435/287.3; 435/809; 435/305.2; 435/307.1; 435/309.2; 435/286.2; 435/286.5; 422/26; 422/28; 312/236; 414/273; 414/281

(58) Field of Classification Search .............. 435/307.1, 435/809, 286.1, 303.1, 287.3, 305.2, 309.2, 435/286.2, 286.5; 312/236; 422/26, 28; 414/273, 281
See application file for complete search history.

(56) References Cited

U.S. PATENT DOCUMENTS
2,244,082 A * 6/1941 Reyniers ...................... 600/21
(Continued)

FOREIGN PATENT DOCUMENTS
WO WO 2004/011593 2/2004
WO WO-2004/011593 A1 2/2004

OTHER PUBLICATIONS
European Search Report received in EPO Application No. 05256595.9, dated Mar. 8, 2006.

*Primary Examiner*—Nathan A Bowers
(74) *Attorney, Agent, or Firm*—Marshall, Gerstein & Borun LLP

(57) ABSTRACT

To present an automatic cell cultivation apparatus capable of sterilizing completely including a cold storage unit and a normal temperature storage unit, without causing cross contamination, in used of cell cultivation of plural subjects. An automatic cell cultivation apparatus comprising an operation unit 11 for operating to cultivate cells of subjects, incubator units 14 for cultivating the cells, a cold storage unit 16 for storing reagents necessary for cultivation, a normal temperature storage unit 17 for storing culture tools, an inlet-outlet unit 15 for taking in and out reagents and culture tools, and a steam supply unit 22 for autoclave sterilization, in which the incubator units 14, the cold storage unit 16, the normal temperature storage unit 17, and the inlet-outlet unit 15 communicate with the operation unit 11, and have sealing doors 18a to 18d leading to the operation unit 11, filters 20a and 20b for cleaning and sterilizing the air stream supplied in the operation unit 11 are provided, and sealing doors 30a and 30b are provided between the filter units and the operation unit 11. By selecting the sealing doors 18a to 18d and opening and closing, sterilizing steam from the steam supply unit 22 is supplied into any of the sterilization required units, operation unit 11, and the incubator units 14, the cold storage unit 16, the normal temperature storage unit 17, and the inlet-outlet unit 15, communicating with the operation unit 11.

2 Claims, 6 Drawing Sheets

U.S. PATENT DOCUMENTS

| | | |
|---|---|---|
| 4,154,652 A | 5/1979 | Sawamura et al. |
| 5,360,741 A * | 11/1994 | Hunnell .................. 435/287.2 |
| 6,508,989 B1 * | 1/2003 | Urrusti et al. ............... 422/121 |
| 2002/0090320 A1 * | 7/2002 | Burow et al. .................. 422/64 |
| 2003/0040104 A1 | 2/2003 | Barbera-Guillem |
| 2004/0152186 A1 * | 8/2004 | Kan et al. ................ 435/286.6 |
| 2004/0215362 A1 * | 10/2004 | Kokubo et al. .............. 700/130 |

* cited by examiner

AUTOMATIC CELL CULTIVATION APPARATUS UTILIZING AUTOCLAVE STERILIZATION AND METHOD FOR USING THE SAME

The present application claims the benefit of priority of Japanese Patent Application No. 2004-309295 filed Oct. 25, 2004. The entire text of the priority application is incorporated herein by reference in its entirety.

FIELD OF THE INVENTION

The present invention relates to an automatic cell cultivation apparatus utilizing autoclave sterilization and a method of using the same, and more particularly to an automatic cell cultivation apparatus utilizing autoclave sterilization and a method of using the same, capable of sterilizing completely including the storage units without causing cross contamination even if used in cell cultivation of plural subjects.

BACKGROUND OF THE INVENTION

Recently, so-called regenerative medicine, taking out a part of human body such as cells and tissues of skin, cartilage, bone, blood vessel, and organs, cultivating outside the body, and using in treatment of the same subject or a different patient, is developed and partly put in use. In such regenerative medicine, a small amount of cells sampled from human body is cultivated outside the body, and in such cell cultivation, it is most important to prevent contamination of cultured cells. In particular, when cultivating cells of plural subjects simultaneously, it is an important problem how to prevent from cross contamination, such as getting mixed in with cells of other subjects during incubation, or infectious bacteria, virus or mycoplasma etc. sticking to the cells.

On the other hand, for practical application of regenerative medicine, safe and inexpensive cell culture is demanded, and necessity is being discussed about automatic apparatus for operating the steps of incubation, culture medium exchange, and subculture until end of cell cultivation repeatedly and automatically. For automating such cultivation operation, in order to avoid the problem of cross contamination, at the present, one cell cultivation apparatus is used exclusively until the completion of cell cultivation for one subject, or the cultivation apparatus is used under incomplete contamination countermeasures using downflow air stream, but the problems are not solved sufficiently.

That is, when using one cell cultivation apparatus exclusively for one subject, cells of other subjects do not exist in the apparatus, and there is no problem of cross contamination during cultivation. However, the cost is higher from the viewpoint of efficiency of use of apparatus. In the cultivation apparatus using downflow air stream, cells of other subjects may exist in the apparatus, and contamination of containers for other subjects with such cells, bacteria, virus or mycoplasma cannot be prevented completely, and these are not sufficient countermeasures of problems of cross contamination.

To solve these problems, an apparatus has been developed for cultivating cells of plural subjects while preventing cross contamination (see International Publication No. 2004/011593 pamphlet FIG. 2). This automatic cultivation apparatus comprises a plurality of incubator units, and an operation unit commonly used for culture operation such as culture medium exchange and subculture. After end of culture operation of one subject, the apparatus is sterilized by ozone or other gas, but if the residual gas exists in the apparatus, the cells to be incubated may be destroyed. This automatic cultivation apparatus can sterilize the incubator units and the operation unit in the apparatus main body, but cannot sterilize the storage units storing reagents and culture tools used in cultivation, or the inlet-outlet unit for bringing in and out the reagents and culture tools. Therefore, cross contamination cannot be prevented completely including the storage units and the inlet-outlet unit.

The present invention is devised to solve the problems of the related art, and it is hence an object of the invention to present an automatic cell cultivation apparatus capable of sterilizing completely including the storage units and the inlet-outlet unit, without causing cross contamination, if used in cell cultivation of plural subjects.

SUMMARY OF THE INVENTION

To solve the problems, the automatic cell cultivation apparatus utilizing autoclave sterilization of the invention comprises an operation unit for conducting operations necessary to cultivate cells of subjects, one or more incubator units for cultivating the cells, one or more storage units for storing reagents and tools necessary for cultivation, and a steam supply unit for autoclave sterilization, wherein the incubator units and storage units communicate with the operation unit and have sealing doors leading to the operation unit, respectively, and by selecting the sealing door and opening or closing, sterilizing steam from the steam supply unit is supplied into the operation units, and any of the selected incubator units and the selected storage units communicating with the operation unit.

In the automatic cell cultivation apparatus of the invention, since autoclave sterilization is employed, unlike gas sterilization, there is no risk of residual gas, and sterilization is completed in a short time. Besides, autoclave sterilization is employed in sterilization apparatus usually used in hospitals and other clinical institutions, and sterilization effect is high and cross contamination can be prevented securely.

The incubator units and the storage units communicating with the operation unit can be opened to the operation unit by opening the sealing doors, and can be sterilized together with the operation unit when sterilization is needed.

The automatic cell cultivation apparatus further comprises an inlet-outlet unit for putting in and taking out reagents and culture tools, and the inlet-outlet unit communicates with the operation unit, and has a sealing door leading to the operation unit, and by opening and closing the sealing door, sterilizing steam from the steam supply unit is supplied. Thus, by opening the sealing door, the inlet-outlet unit communicates with the operation unit, and it can be sterilized together with the operation unit when sterilization is needed.

The automatic cell cultivation apparatus further comprises a filter unit for cleaning and sterilizing air stream supplied into the operation unit, and a sealing door installed between the filter unit and the operation unit, and the filter unit is isolated from the operation unit at the time of autoclave sterilization.

Therefore, the filter unit is protected from heat or steam during autoclave sterilization.

The operation unit may include an operation robot, a centrifugal separator, and cultivation operation devices necessary for cultivating cells, and the operation unit may include a device installation unit installing the operation robot and centrifugal separator, and a cultivation operation unit installing the cultivation operation devices, and a shut-off device may be provided between the device installation unit and the cultivation operation unit. Thus, only the cultivation operation unit can be sterilized.

In the invention, the cultivation operation device necessary for cultivating cells may include a turntable, a pipetting device, and a centrifugal tube handling device, and the operation necessary to cultivate cells may include culture medium exchange operation and subculture operation.

The method to use the automatic cell cultivation apparatus of the invention is a method for using any one of automatic cell cultivation apparatuses mentioned above, and is comprising the steps of cultivating the cells for one subject, then closing all sealing doors, and sterilizing the operation unit only.

Thus, cells of plural subjects can be cultivated individually in the incubator units, cells of one subject in one incubator unit, and individual cultivation operations for plural subjects can be carried out by a common operation unit while preventing cross contamination.

The method of using automatic cell cultivation apparatus of the invention is also a method for use any one of automatic cell cultivation apparatuses mentioned above, and comprises the steps of finishing the cell culture for one subject, then opening the sealing door between the incubator unit of the subject and the operation unit, closing all other sealing doors, and sterilizing the incubator unit of the subject and the operation unit only.

Thus, the incubator units can be used independently for plural subjects, and the utilization efficiency of automatic cell cultivation apparatus can be enhanced.

The method for use automatic cell cultivation apparatus of the invention is also a method to use for maintenance of the automatic cell cultivation apparatuses mentioned above, and comprises opening the sealing doors between the operation unit and the incubator units requiring sterilization and the sealing doors between the operation unit and the storage units requiring sterilization, and sterilizing the incubator units and the storage units together with the operation unit, simultaneously.

Therefore, maintenance is easily attained in internal parts to be sterilized in the automatic cell cultivation apparatus.

In another aspect of the invention, the method for use an automatic cell cultivation apparatus, comprising the steps of opening the sealing door between the inlet-outlet unit and the operation unit, and sterilizing the inlet-outlet unit together with the operation unit, simultaneously.

In the automatic cell cultivation apparatus having a shut-off device provided between the device installation unit and the cultivation operation unit, by closing this shut-off device, only the cultivation operation unit can be sterilized.

In the automatic cell cultivation apparatus of the invention, since autoclave sterilization is employed, unlike gas sterilization, there is no risk of residual gas, and sterilization is completed in a short time. Besides, autoclave sterilization is employed, and a high sterilization effect is expected same as in a sterilization apparatus usually used in hospitals and other clinical institutions.

Moreover, by opening and closing sealing doors selectively, only the necessary parts can be sterilized for every subject or for every cultivation operation, and cells of plural subjects can be cultivated by one apparatus, while cross contamination can be securely prevented.

EMBODIMENTS

The automatic cell cultivation apparatus utilizing autoclave sterilization of the invention and the method of manufacturing the same will be explained below while referring to the accompanying drawings, but the invention is not limited to the following explanation.

Figure 1:
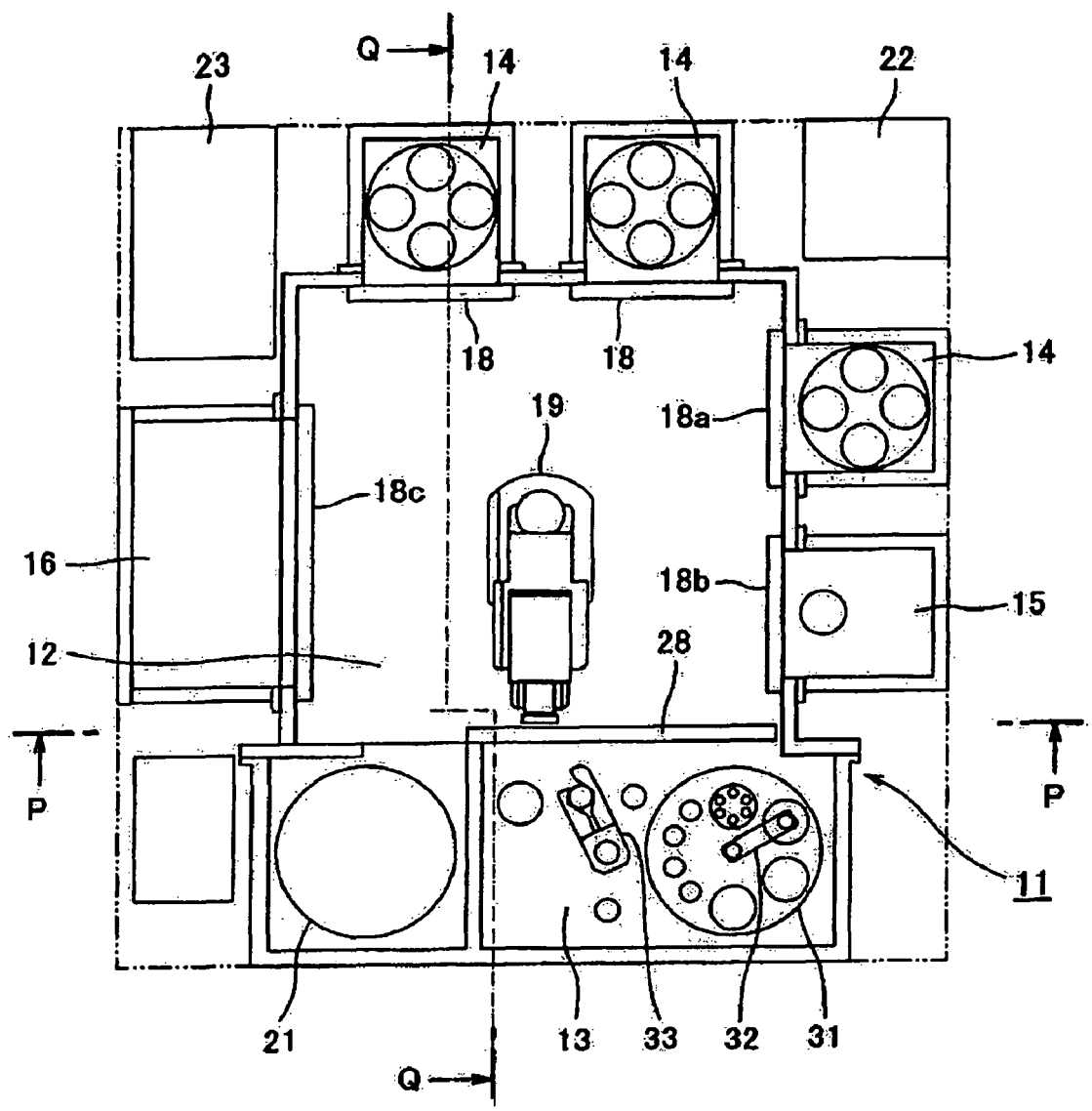
FIG. 1 is a plan view of automatic cell cultivation apparatus of an embodiment of the present invention.
Figure 2:
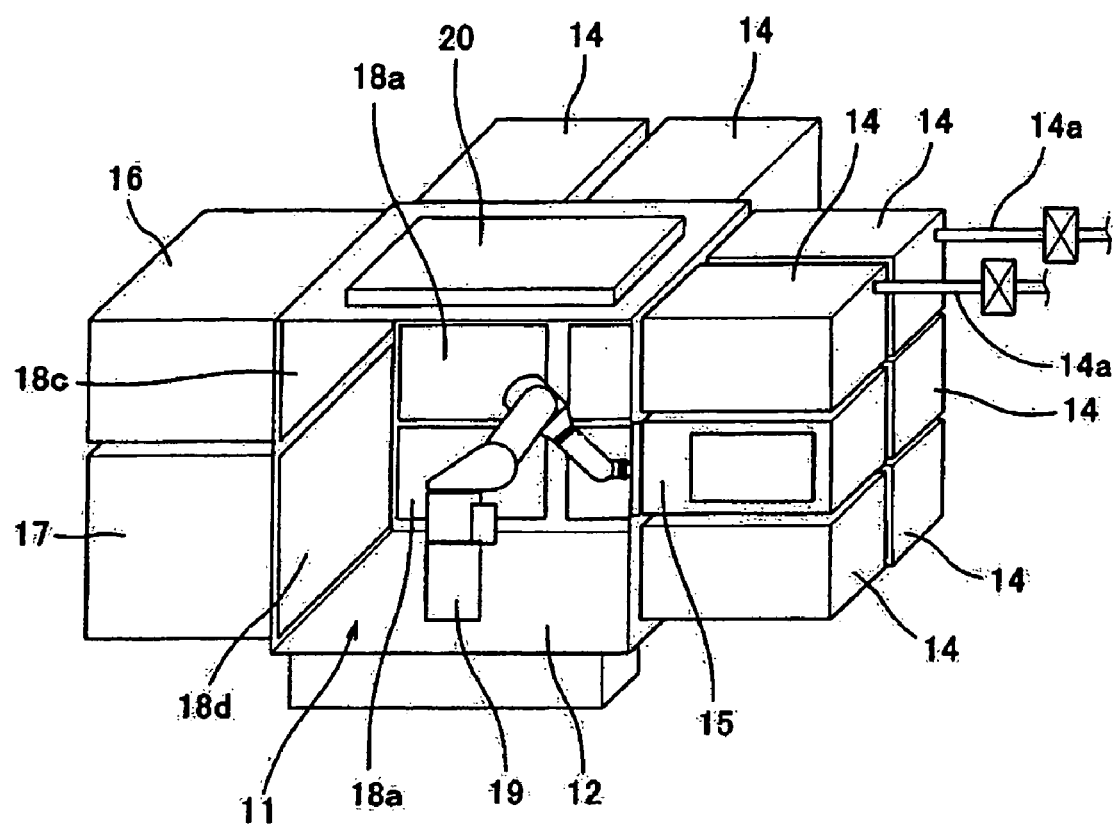
FIG. 2 is a perspective view cut away by line P-P of FIG. 1 as seen from upper right side of the direction indicated by the arrows.
Figure 3:
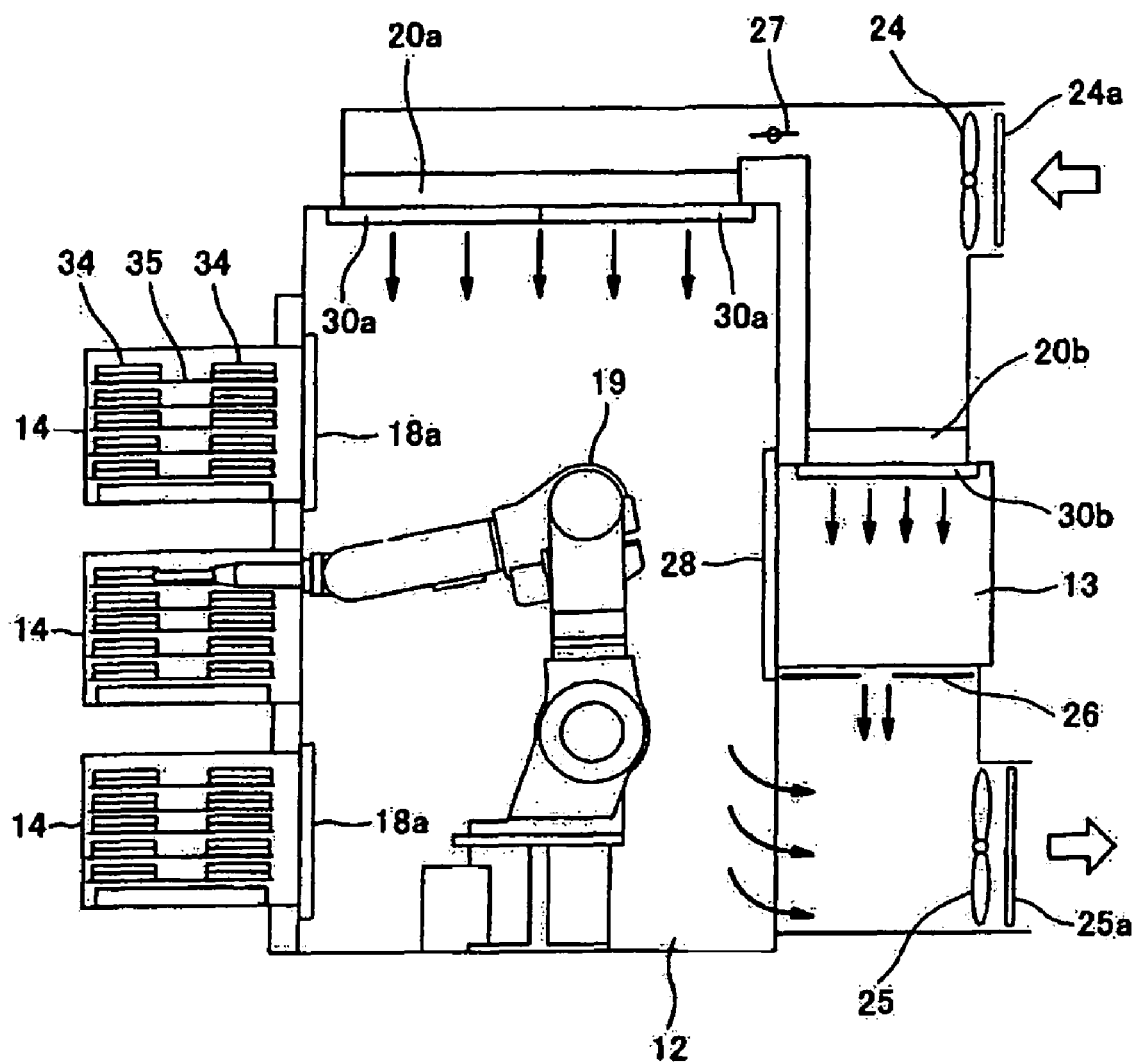
FIG. 3 is a cross-sectional view taken in the direction of arrows substantially along the line Q-Q of FIG. 1.
Figure 4:
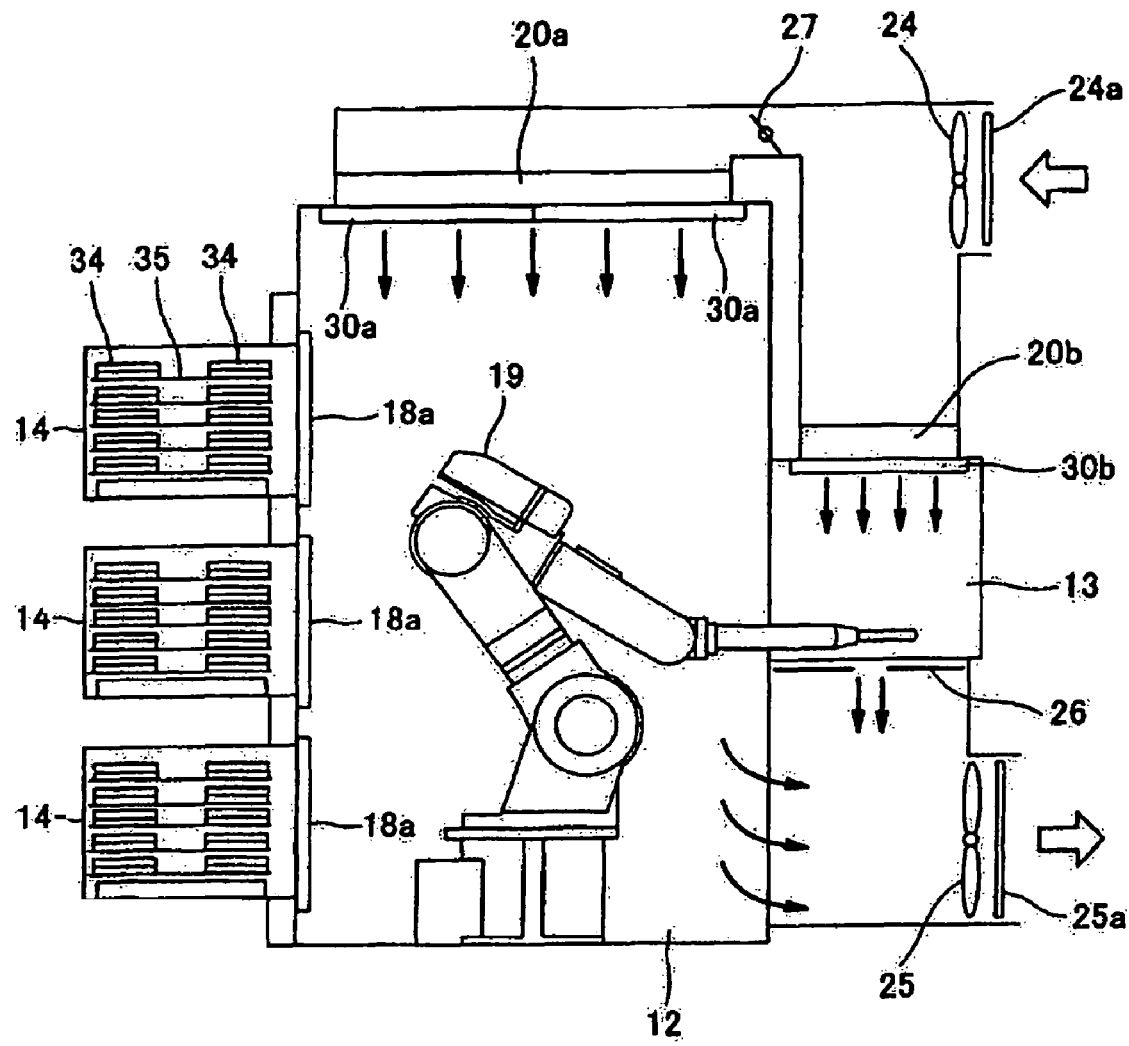
FIG. 4 is a cross-sectional view taken in the direction of arrows substantially along the line Q-Q of FIG. 1.

FIG. 1 is a plan view of automatic cell cultivation apparatus in an embodiment of the invention, and FIG. 2 is a perspective view cut away by line P-P of FIG. 1 as seen from upper right side of the direction indicated by the arrows. FIGS. 3 and 4 are cross-sectional views taken in the direction of arrows substantially along the line Q-Q of FIG. 1. As shown in FIGS. 1 and 2, the automatic cell cultivation apparatus of the invention comprises an operation unit 11, a plurality of incubator units 14, a cold storage unit 16 and a normal temperature storage unit 17 as storage units, an inlet-outlet unit 15, and a steam supply unit 22.

The operation unit 11 is a space for cultivation operation necessary for cultivating cells of subjects, and is composed of a cultivation operation unit 13 and a device installation unit 12 other than the unit 13, as shown in FIG. 1. The cultivation operation unit 13 includes, as shown in FIG. 1, a turntable 31, a pipetting device 32, a centrifugal tube handling device 33, and a used medicine disposal unit not shown. The device installation unit 12 includes an operation robot 21 that carries an actual cultivation operations on behalf of human resources, and a centrifugal separator 21. The operation robot 19, centrifugal separator 21, turntable 31, pipetting device 33 and centrifugal handling device 33 are operated under control of a controller 23 shown in FIG. 1.

The incubator unit 14 is a space for cultivating cells, and as shown in FIGS. 3 and 4, the inside of each of the incubator unit 14 has a multi-stage dish rack 35 for holding a multiplicity of Petri dishes 34 used in cell cultivation. Also as shown in FIG. 1, each incubator unit 14 is connected to a piping 14a for supplying carbon dioxide gas for adjusting the culture atmosphere. Although only two pipings 14a are shown in FIG. 2, actually pipings 14a for supplying carbon dioxide gas are connected to all of the incubator units 14. In this embodiment, culture cells cultivated in one incubator unit 14 is limited to one subject only, and culture cells derived from different subjects can be cultivated in each incubator unit 14.

The cold storage unit 16 is equipped to refrigerate reagents necessary for cultivation, and examples of the reagents include culture medium, trypsin solution for exfoliating the cultured cells, etc. Sterilized reagents are stored in the cold storage unit 16.

The normal temperature storage unit 17 is equipped to store culture tools used in cell cultivation and chemicals to be stored at ordinary temperature, and such culture tools include pipettes used in exchange of culture medium and centrifugal tubes. The normal temperature storage unit 17 stores already sterilized culture tools. The normal temperature storage unit 17 further stores chemicals to be stored at ordinary temperature (for example, phosphate buffer solution (PBS), and physiological saline).

The inlet-outlet unit 15 is equipped for taking in and out the cells to be cultivated, cells after cultivation, reagents and culture tools. The inlet-outlet unit may be also used as inlet of cells to be cultivated and outlet after cultivation.

The steam supply unit 22 is equipped for supplying steam for autoclave sterilization, and, for example, saturated steam (sterilizing steam) at 121 deg. C. can be supplied.

In this embodiment, a plurality of incubator units 14 and one inlet-outlet unit 15 are fixed to the operation unit 11 to form a plurality of vertical rows provided in three stages vertically, as shown in FIG. 2. The inlet-outlet unit 15 is located in the middle of vertical rows of three vertical stages, as shown in FIG. 2. The cold storage unit 16 and the normal temperature storage unit 17 form vertical rows in two vertical stages, and the cold storage unit 16 is located at the upper stage and the normal temperature storage unit 17 is located at the lower stage.

In the automatic cell cultivation apparatus of the embodiment has, as shown in FIG. 2 to FIG. 4, a filter unit 20a is provided above the device installation unit 12 of the operation unit 11, and a filter unit 20b is provided above the cultivation operation unit 13. The filter units 20a and 20b have HEPA filters (high efficiency particulate air filters).

In the apparatus of the invention, a sealing door 18a of an automatically opening and closing type is provided between the operation unit 11 and the incubator unit 14, a sealing door 18b of an automatically opening and closing type is provided between the operation unit 11 and the inlet-outlet unit 15, a sealing door 18c of an automatically opening and closing type is provided between the operation unit 11 and the cold storage unit 16, and a sealing door 18d of an automatically opening and closing type is provided between the operation unit 11 and the normal temperature storage unit 17. Further as shown in FIG. 3 and FIG. 4, between the filter unit 20a and the device installation unit 12, and between the filter unit 20b and the cultivation operation unit 13, sealing doors 30a and 30b of an automatically opening and closing type are provided respectively. Further, between the device installation unit 12 and the cultivation operation unit 13 of the operation unit 11, a shutter 28 is provided as a shut-off device. These sealing doors 18a to 18d, 30a and 30b and the shutter 28 are made of materials of high air tightness and heat insulation, and during autoclave sterilization, leak of steam from operation unit 10 is prevented, and heat conduction from the operation unit 11 is suppressed as much as possible.

Therefore, while the sealing doors 18a to 18d are open, the incubator unit 14, the inlet-outlet unit 15, the cold storage unit 16, and the normal temperature storage unit 17 communicate with the operation unit 11 spatially, and are sterilized together with the operation unit 11 by the steam from the steam supply unit 22, whereas when the sealing doors 18a to 18d are closed, the incubator unit 14, the inlet-outlet unit 15, the cold storage unit 16, and the normal temperature storage unit 17 are almost completely isolated from the operation unit 11, and are free from effects of sterilizing steam. When the sealing doors 30a and 30b of the filter units 20a and 20b are closed when sterilizing the operation unit 11, the filter units 20a and 20b are protected from sterilizing steam. Further, by closing the shutter 28, only the device installation unit 12 or only the sterilization operation unit 13 can be sterilized. In this embodiment, opening or closing of sealing doors 18a to 18d, 30a and 30b, and opening and closing of shutter 28 are also controlled by the controller 23.

As shown in FIG. 3 and FIG. 4, in this embodiment, downflow air stream is supplied by an intake fan 24 and an exhaust fan 25 into the device installation unit 12 and sterilization operation unit 13 of the operation unit 11. This air stream is sucked by the intake fan 24 through a pre-filter 24a, the majority of which is subjected to dust-elimination by the filter unit 20a and supplied into the device installation unit 12, and exhausted outside by the exhaust fan 25 from beneath the cultivation operation unit 13 through a pre-filter 25a. Part of the air stream sucked by the intake fan 24 is subjected to dust-elimination by the filter unit 20b, and supplied into the cultivation operation unit 13, and exhausted outside by the exhaust fan 25 from beneath the device installation unit 12. The air stream passing through the filter 25a can be, without being discarded outside, later passed into the HEPA filter 20a or 20b through the intake filter 24a, and then returned to the apparatus, so that an internal circulation loop may be formed. The amount of air stream supplied in the device installation unit 12 and sterilization operation unit 13 is adjusted by the shutter 26 and damper 27.

In the apparatus of the embodiment, culture medium exchange operation and subculture operation necessary for cell cultivation are performed automatically. In the automatic cell cultivation apparatus of the embodiment, culture medium exchange operation is performed as follows. First, as shown in FIG. 3, the operation robot 19 takes out the Petri dish 34 under cell-cultivation placed in the dish rack 35 within the incubator 14, turn around the direction toward the cultivation operation unit 13 as shown in FIG. 4, and moves the Petri dish 34 onto the turntable 31 of the cultivation operation unit 13. Next, the operation robot 19 opens the lid of Petri dish 34. In succession, the pipetting device 32 sucks the culture medium in the Petri dish and discards, and supplies a new culture medium into the Petri dish. The operation robot 19 closes the lid of the Petri dish 34, and returns to the initial position in the dish rack 35 in the incubator unit 14. This series of operation is conducted under control of the controller 23.

Next, the subculture operation in the automatic cell cultivation apparatus of the embodiment is as follows. First, in the same manner as mentioned above, the operation robot 19 takes out the Petri dish 34 under cell-cultivation placed in the dish rack 35 within the incubator 14, moves the Petri dish 34 onto the turntable 31 of the cultivation operation unit 13, and opens the lid of Petri dish 34, and the pipetting device 32 sucks the broth in the Petri dish and discards. The pipetting device 32 drops trypsin solution for exfoliating the cultured cells from the Petri dish. The operation robot 19 inclines and rotates the Petri dish, so that the trypsin solution is distributed all over the Petri dish 34. When the cells are exfoliated from the Petri dish as being monitored by a TV camera or the like (not shown), the pipetting device 32 transfers the solution containing cells in the Petri dish 34 to a centrifugal tube held by the centrifugal tube handling device 33. The centrifugal tube handling device 33 caps the centrifugal tube, sets it in the centrifugal separator 21. When centrifugal separation by centrifugal separator 21 is terminated, the centrifugal tube handling device 33 detaches the cap from the centrifugal tube. The pipetting device 32 discards the supernatant in the centrifugal tube, sucks out the cells settling in the bottom of the centrifugal tube, and dispenses into a plurality of new Petri dishes on the turntable 31 by small portions. The operation robot 19 closes lids of these Petri dishes, and puts one by one in the dish rack 35 in the incubator 14, and their positions are stored in the controller 23 for next culture medium exchange operation and subculture operation.

In the automatic cell cultivation apparatus of the embodiment, autoclave sterilization is conducted after cultivation operation for one subject, after completion of cell cultivation for one subject, at the time of maintenance of automatic cell cultivation apparatus, and when carrying culture cells, reagents, and culture tools in and out of the apparatus. Method of autoclave sterilization using the automatic cell cultivation apparatus of the embodiment will be explained.

Figure 5:
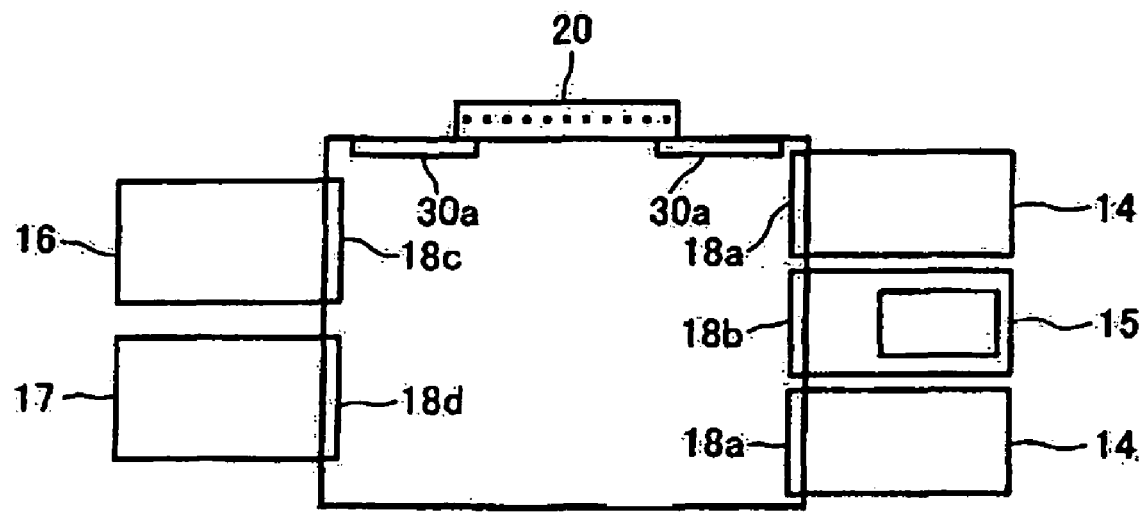
FIG. 5 is a cross-sectional view taken in the direction of arrows substantially along the line P-P of FIG. 1.
Figure 6:
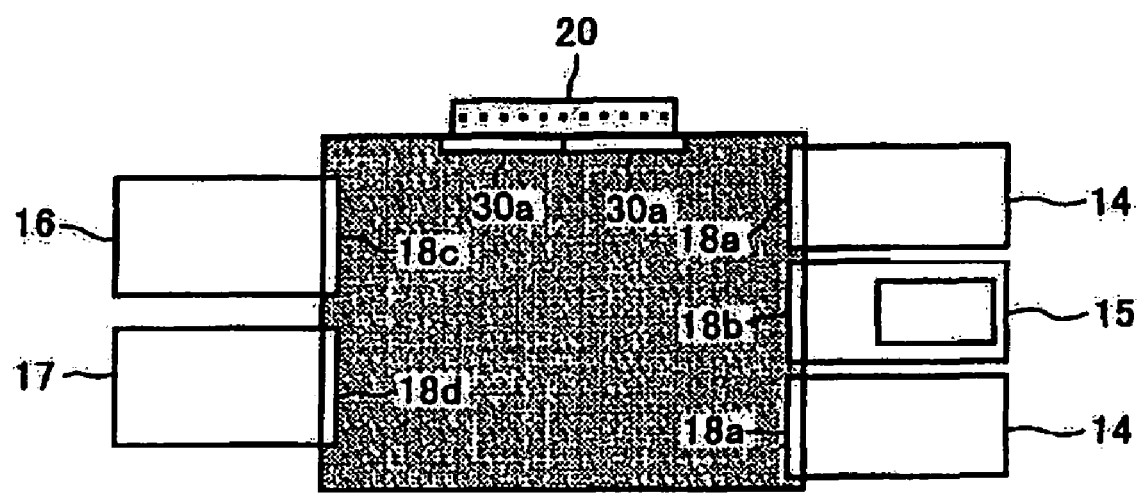
FIG. 6 shows a case where sterilizing steam is supplied into operation unit 11 from steam supply unit 22 in FIG. 5.
Figure 7:
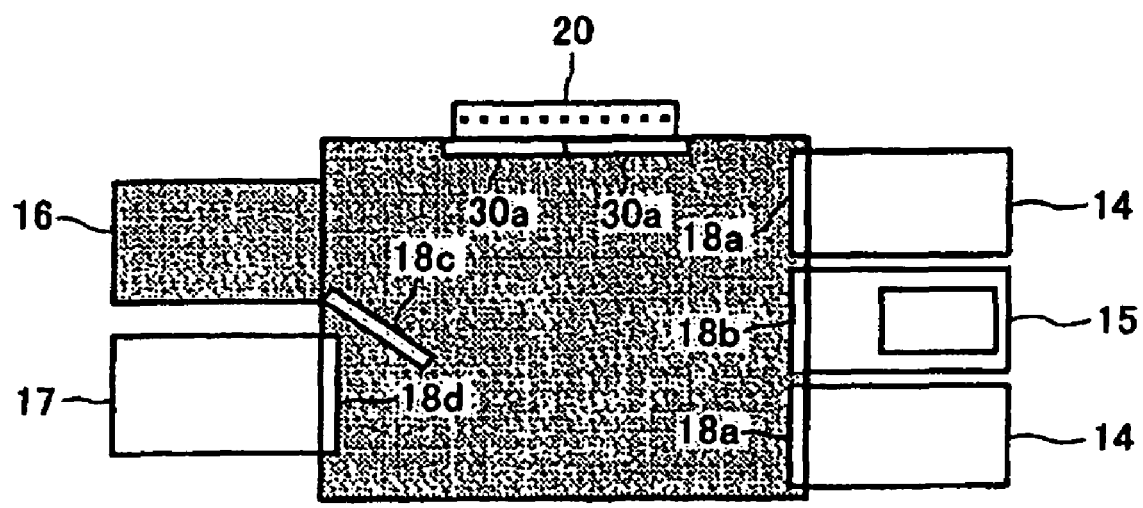
FIG. 7 is an arrow sectional view along line P-P of FIG. 1, showing a case where cold storage unit 16 and operation unit 11 are sterilized.

FIG. 5 to FIG. 7 are cross-sectional views taken in the direction of arrows substantially along the line P-P of FIG. 1, and in these drawings, the operation robot is omitted. After cultivation operation for one subject such as culture medium exchange operation or subculture operation, autoclave sterilization is executed in the following procedure before starting cultivation operation for another subject. In this case, only the operation unit 11 is to be sterilized, and the sealing door 18a of each incubator unit 14, the sealing door 18b of the inlet-outlet unit 15, the sealing door 18c of the cold storage unit 16, the sealing door 18d of the normal temperature storage unit 17, and the sealing doors 30a and 30b of the filters 20a and 20b are closed. Then, saturated steam at, for example, 121 deg. C. is supplied from the steam supply unit 22 to the operation unit 11 (FIG. 6). At this time, since the sealing doors 18a to 18d have high air tightness and heat insulation as mentioned above, culture cells in the incubators 14, and reagents and culture tools stored in the cold storage unit 16 and the normal temperature storage unit 17 are not damaged. After a sufficient time for sterilization, steam supply is stopped, and when the operation unit 11 returns to ordinary temperature, cell cultivation operation for next subject can be started.

Next, autoclave sterilization conducted after completion of cell cultivation for one subject will be explained. This sterilization is conducted after taking out culture cells, upon completion of cultivation to specified degree by repeating cultivation operations of culture medium exchange operation and subculture operation. In this case, because only the operation unit 11 and a specific incubator unit 14 must be sterilized, the sealing door 18a of the incubator unit 14 is opened and all other sealing doors 18a to 18d, and the sealing doors 30a and 30b are closed. Next, saturated steam at, for example, 121 deg. C. is supplied from the steam supply unit 22. At this time, since the sealing door 18a of the incubator 14 to be sterilized is opened, only the operation unit 11 and the incubator unit 14 are sterilized by the sterilizing steam. After a sufficient time for sterilization, steam supply is stopped, and when the incubator unit 14 and the operation unit 11 return to ordinary temperature, cell cultivation operation for other subject can be started by using the sterilized incubator unit 14.

Further, autoclave sterilization is conducted also at the time of maintenance of automatic cell cultivation apparatus. In the sterilization of this case, either one or both of the sealing door 18c of the cold storage unit 16 and the sealing door 18d of the normal temperature storage unit 17, and the sealing door 18a of the incubator unit 14 to be sterilized are opened, and all other sealing doors 18a and 18b, and the sealing doors 30a and 30b are closed. In this state, saturated steam at, for example, 121 deg. C. is supplied from the steam supply unit 22. As a result, the operation unit 11, the cold storage unit 16, the normal temperature storage unit 17, and the incubator unit 14 to be sterilized are sterilized at the same time. FIG. 7 shows a case of sterilizing the cold storage unit 16 and the operation unit 11 only, without sterilizing the incubator unit 14 and the normal temperature storage unit 17.

In the automatic cell cultivation apparatus of the embodiment, the inlet-outlet unit 15 is also sterilized occasionally. The inlet-outlet unit 15 can be sterilized by opening the sealing door 18b of the inlet-outlet unit 15, properly when putting culture cells, reagents and culture tools in the apparatus, or when taking them out, and the sterilization can be conducted at the same time of sterilization of operation unit 11 after cultivation operation, sterilization of operation unit 11 and incubator unit 14 upon completion of cell cultivation for one subject, and sterilization at the time of maintenance of automatic cell cultivation apparatus.

In addition, in the automatic cell cultivation apparatus of the embodiment, since the shutter 28 is provided between the device installation unit 12 and the cultivation operation unit 13, when the sterilizing steam from the steam supply unit 22 is introduced only into the cultivation operation unit 13, by closing the shutter 28, only the cultivation operation unit 13 can be sterilized. Alternatively, when the sterilizing steam from the steam supply unit 22 is introduced only into the device installation unit 12, by closing the shutter 28, only the device installation unit 12 can be sterilized.

Moreover, in the automatic cell cultivation apparatus of the embodiment, the entire of the interior can be sterilized. That is, by closing the sealing doors 30a and 30b and opening all sealing doors 18a to 18d, the device installation unit 12 and the cultivation operation unit 13 of the operation unit 11, the incubator unit 14, the inlet-outlet unit 15, the cold storage unit 16, and the normal temperature storage unit 17 can be sterilized simultaneously.

According to the automatic cell cultivation apparatus employing autoclave sterilization of the invention and the method of using the same, cell cultivation can be operated automatically, and it can be effectively applied in the field of regeneration medicine.

What is claimed is:

1. An automatic cell cultivation apparatus comprising:
   an operation unit, the operation unit comprising a central space and including a plurality of devices for the cultivation of cells;
   a plurality of units, the units comprising a plurality of incubator units and a storage unit;
   a steam supply unit in flow communication with the operation unit and arranged to supply steam to the central space of the operation unit for sterilization;
   a first one of the plurality of incubator units arranged to incubate cells of a first subject;
   a second one of the plurality of incubator units arranged to incubate cells of a second subject different than the first subject;
   each of the plurality of incubator units and the storage unit including an insulated sealing door, each sealing door selectively shiftable between an open position in which each selected unit is in spatial communication with the operation unit and a closed position in which leakage between each selected unit and the operation unit is prevented;
   a controller operatively coupled to the steam supply unit and the insulated sealing doors and arranged to bring the steam supply unit into flow communication with the operation unit and further arranged to shift the selected sealing doors between the open and closed positions;
   wherein by maintaining all of the sealing doors in the closed position the steam supply unit can be brought directly into flow communication with only the central space of the operation unit, and further wherein by selectively shifting one or more of the sealing doors to the open position the steam supply unit can be brought into flow communication with only the units associated with the selected doors, thereby permitting access to and sterilization of each incubator unit while preventing cross contamination between the first incubator unit and the second incubator unit; and further comprising an air intake and an air exhaust defining an internal circulation loop through the operation unit;

wherein the operation unit includes a device installation unit and a cultivation operation unit, the device installation unit including a robot, the operation unit further including an insulated sealing shutter shiftable between an open position in which the cultivation operation unit is in spatial communication with the device installation unit and a closed position in which leakage between the device installation unit and the cultivation operation unit is prevented;

wherein the air circulation loop includes an insulated sealing door arranged to block or permit air flow into the operation unit, the air circulation loop further including a shutter associated with the cultivation operation unit and arranged to provide flow communication between the cultivation operation unit and the air exhaust; and wherein the cultivation operation unit is in flow communication with the steam supply unit, and wherein when the sealing shutter is in the closed position steam from the steam supply unit can be introduced to into the cultivation operation unit only.

2. An automatic cell cultivation apparatus comprising:

an operation unit, the operation unit comprising a central space and including a plurality of devices for the cultivation of cells;

a plurality of units, the units comprising a plurality of incubator units and a storage unit;

a steam supply unit in flow communication with the operation unit and arranged to supply steam to the central space of the operation unit for sterilization;

a first one of the plurality of incubator units arranged to incubate cells of a first subject;

a second one of the plurality of incubator units arranged to incubate cells of a second subject different than the first subject;

each of the plurality of incubator units and the storage unit including an insulated sealing door, each sealing door selectively shiftable between an open position in which each selected unit is in spatial communication with the operation unit and a closed position in which leakage between each selected unit and the operation unit is prevented;

a controller operatively coupled to the steam supply unit and the insulated sealing doors and arranged to bring the steam supply unit into flow communication with the operation unit and further arranged to shift the selected sealing doors between the open and closed positions;

wherein by maintaining all of the sealing doors in the closed position the steam supply unit can be brought directly into flow communication with only the central space of the operation unit, and further wherein by selectively shifting only a single additional selected one of the sealing doors to the open position the steam supply unit can be brought into flow communication with only the unit associated with the single additional selected one of the sealing doors, thereby permitting access to and sterilization of each incubator unit while preventing cross contamination between the first incubator unit and the second incubator unit; and further comprising an air intake and an air exhaust defining an internal circulation loop through the operation unit;

wherein the operation unit includes a device installation unit and a cultivation operation unit, the device installation unit including a robot, the operation unit further including an insulated sealing shutter shiftable between an open position in which the cultivation operation unit is in spatial communication with the device installation unit and a closed position in which leakage between the device installation unit and the cultivation operation unit is prevented;

wherein the air circulation loop includes an insulated sealing door arranged to block or permit air flow into the operation unit, the air circulation loop further including a shutter associated with the cultivation operation unit and arranged to provide flow communication between the cultivation operation unit and the air exhaust; and wherein the cultivation operation unit is in flow communication with the steam supply unit, and wherein when the sealing shutter is in the closed position steam from the steam supply unit can be introduced to into the cultivation operation unit only.

* * * * *